(12) United States Patent
Nakatani et al.

(10) Patent No.: US 8,323,572 B2
(45) Date of Patent: Dec. 4, 2012

(54) MEASURING DEVICE

(75) Inventors: Masaya Nakatani, Hyogo (JP); Levent Yobas, Hong Kong (CN); Julien Reboud, Glasgow (GB)

(73) Assignees: Panasonic Corporation, Osaka (JP); Agency for Science Technology and Research, Singapore (SG)

( * ) Notice: Subject to any disclaimer, the term of this patent is extended or adjusted under 35 U.S.C. 154(b) by 0 days.

(21) Appl. No.: 13/445,186

(22) Filed: Apr. 12, 2012

(65) Prior Publication Data

US 2012/0213671 A1    Aug. 23, 2012

Related U.S. Application Data

(63) Continuation of application No. PCT/JP2010/006024, filed on Oct. 8, 2010.

(30) Foreign Application Priority Data

Oct. 13, 2009    (JP) .................................. 2009-236238

(51) Int. Cl.
*G01N 27/00*    (2006.01)
(52) U.S. Cl. .................. 422/82.01; 422/82.02; 422/502; 422/503; 436/150
(58) Field of Classification Search ............... 422/82.01, 422/82.02, 502, 503; 436/150
See application file for complete search history.

(56) References Cited

U.S. PATENT DOCUMENTS

| | | | |
|---|---|---|---|
| 6,541,213 B1 * | 4/2003 | Weigl et al. .................. | 435/7.1 |
| 2004/0072278 A1 | 4/2004 | Chou et al. | |
| 2004/0224380 A1 | 11/2004 | Chou et al. | |
| 2004/0229349 A1 | 11/2004 | Daridon | |
| 2007/0155016 A1 | 7/2007 | Lee et al. | |

FOREIGN PATENT DOCUMENTS

| | | |
|---|---|---|
| WO | 03/085379 | 10/2003 |
| WO | 2005/089253 | 9/2005 |
| WO | 2007/108779 | 9/2007 |
| WO | 2007/139511 | 12/2007 |
| WO | 2008/072029 | 6/2008 |

OTHER PUBLICATIONS

English translation of International Preliminary Report on Patentability issued May 24, 2012 in International (PCT) Application No. PCT/JP2010/006024.
International Search Report issued Dec. 14, 2010 in International (PCT) Application No. PCT/JP2010/006024.
Johan Pihi et al., "Microfluidic Gradient-Generating Device for Pharmacological Profiling", Analytical Chemistry, vol. 77, No. 13, pp. 3897-3903, Jul. 1, 2005.

* cited by examiner

*Primary Examiner* — Lyle Alexander
(74) *Attorney, Agent, or Firm* — Wenderoth, Lind & Ponack, L.L.P.

(57) ABSTRACT

A measuring device includes a first substrate; and a second substrate bonded on the first substrate. The second substrate has at least two inflow ports, at least two outflow ports, and an injection port. The two inflow ports, the two outflow ports, and the injection port penetrate the second substrate. The first substrate includes partition wall portions opposing to each other, and forming a first cavity between the partition wall portions, and forming at least two second cavities close against one of the partition wall portions. Each second cavity is provided adjacent to the first cavity. Through holes are provided in the respective partition wall portions to connect the first cavity and the second cavity to each other, and the through holes are adapted to capture an object to-be-tested introduced in the first cavity.

8 Claims, 7 Drawing Sheets

MEASURING DEVICE

This is continuation application of International Patent Application having application No. PCT/JP2010/006024, filed Oct. 8, 2010. The present application claims the priority of Japanese Patent Application No. 2009-236238 filed in Japan on Oct. 13, 2009, the contents of which are hereby incorporated by reference.

BACKGROUND

1. Technical Field

The present invention relates to a measuring device for measuring characteristics of objects to-be-tested formed from cells, films derived from biological bodies, and the like.

2. Background Art

As illustrated in FIG. 8, a cell electrophysiological sensor as an example of a conventional measuring device includes a substrate 1 which is provided with a first cavity 2, and a second cavity 5 connected there between through a through hole 4 provided in a partition wall portion 3.

In this case, the first cavity 2 and the second cavity 5 are filled with respective predetermined electrolytic solutions, further cells 6 are injected into the first cavity 2 and, then, suction and the like is applied thereto from the second cavity 5, which can cause a cell 6 to be trapped (captured) into the opening portion 7 of the through hole 4 at the first cavity 2 side.

Further, in the state where the cell 6 is being trapped therein, a chemical agent is introduced into the first cavity 2, and the electric-potential difference between the electrolytic solutions in the first cavity 2 and the second cavity 5, or the value of the electric current flowing between the first cavity 2 and the second cavity 5 is determined, which enables determining electric-potential changes or electric-current values induced intracellularly and extracellularly during actions of the cells 6, or physicochemical changes induced by actions of the cells.

Further, it is possible to cite prior-art documents as described in WO2007/108779 (Patent Document 1) and WO2007/139511 (Patent Document 2), for example, as those which disclose examples similar to the aforementioned cell electrophysiological sensor.

SUMMARY OF THE INVENTION

Such conventional measuring devices have had the problem of degradation of the measuring efficiency. This is caused by failures of adhesion of objects to-be-tested, which are objects to be measured, errors of absorption of them, time losses due to introduction of measurement solutions and chemical agents, and the like. Namely, in cases of measurement for cells 6 as objects to-be-tested, particularly, it is necessary that a single cell 6 comes into contact with a single through hole 4 with a higher adhesion force. That is, in general, an electrophysiological reaction (for example, an electric-potential difference induced intracellularly and extracellularly, or a value of an electric current flowing intracellularly and extracellularly) is caused in such a cell 6, which is an extremely small reaction. Therefore, when the cell 6 is not in intimate contact with the through hole 4, there is an electrical leak induced through the gap therebetween. Such an electrical leak obstructs accurate measurement of the electrophysiological reaction caused intracellularly and extracellularly.

In general, it is impossible to perform measurement with higher accuracy, for cells having induced adhesion failures as described above, due to noise caused by electric leaks, which prevents acquisition of measurement data. This causes the necessity for performing new measurement from the beginning, using an additionally-prepared measuring device. This results in significant degradation of the efficiency of measurement of electrophysiological reactions of cells.

Further, another cause of degradation of the measurement efficiency is absorption errors, due to unactivated cells, dust rather than cells, and the like. Namely, solid substances existing within measurement solutions may include unactivated cells and dust, as well as cells desired to be measured.

Accordingly, in the case of absorption of them to the through hole 4, it is impossible to acquire measurement data, which causes the necessity for performing new measurement from the beginning, using an additionally-prepared measuring device. This results in significant degradation of the efficiency of electrophysiological measurement for cells.

Further, yet another cause of degradation of the measurement efficiency is measurement time losses caused by time losses due to introductions of measurement solutions and chemical agents. Namely, in such measurement using a conventional measuring device, in general, reactions of cells to a chemical agent of a single type are observed through single measurement. Accordingly, in the case of observing reactions of cells to plural chemical agents, it is necessary to repeatedly perform measurement by performing replacement of the measuring device, thereby requiring a significantly longer time period. This results in significant degradation of the efficiency of measurement of electrophysiological reactions of cells.

Therefore, it is an object of the present invention to overcome the aforementioned problems at the same time for improving the measuring efficiency of a measuring device.

In order to attain the object, a measuring device according to the present invention includes: a first substrate; and a second substrate bonded on the first substrate, the second substrate having at least two inflow ports, at least two outflow ports, and a injection port, wherein the two inflow ports, the two outflow ports, and the injection port penetrate the second substrate, wherein the first substrate includes: partition wall portions opposing to each other, and forming a first cavity between the partition wall portions, and forming at least two second cavities close against one of the partition wall portions, wherein each second cavity is provided adjacent to the first cavity; and through holes provided in the respective partition wall portions to connect the first cavity and the second cavity each other, and the through holes being adapted to capture an object to-be-tested introduced in the first cavity, wherein the first cavity is connected to an external environment through the two inflow ports and the two outflow ports, and the second cavity is connected to the external environment through the injection port.

According to the present invention, it is possible to improve the measurement efficiency of the measuring device. This is because the plural second cavities provided independently of each other enable performing independent measurement on respective objects to-be-tested in the plural through holes.

Further, due to the provision of the at least two inflow ports and the at least two outflow ports, it is possible to perform, at the same time, each measurement on different solutions through single measurement, thereby smoothly performing chemical-agent stimuli thereon. This enables provision of a measuring device with excellent measurement efficiency.

BRIEF DESCRIPTION OF THE DRAWINGS

The present invention will become readily understood from the following description of preferred embodiments thereof made with reference to the accompanying drawings, in which like parts are designated by like reference numeral and in which.

DETAILED DESCRIPTION OF THE PREFERRED EMBODIMENTS

Figure 1:
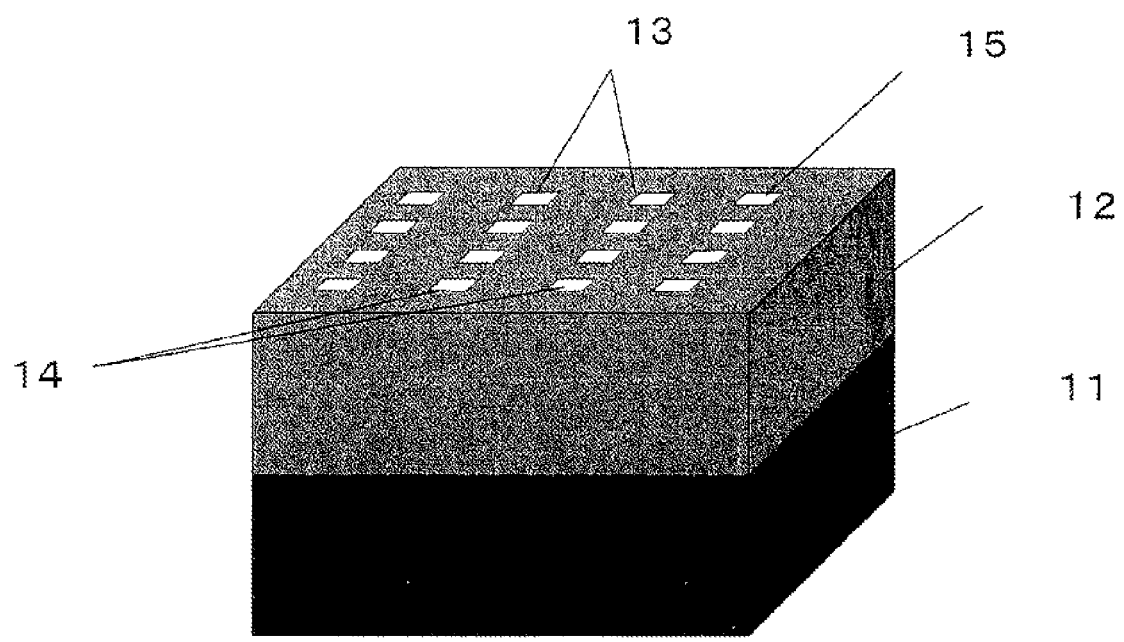
FIG. 1 is a perspective view of a measuring device according to a first embodiment, from there above.

A measuring device according to the present embodiment will be described. Components having the same structures as those in a first embodiment preceding out of respective embodiments will be designated by the same reference characters and will not be described in detail, in some cases. Further, the present invention is not intended to be restricted to the following respective embodiments.

First Embodiment

There will be described the structure of a measuring device according to the present embodiment.

Figure 2:
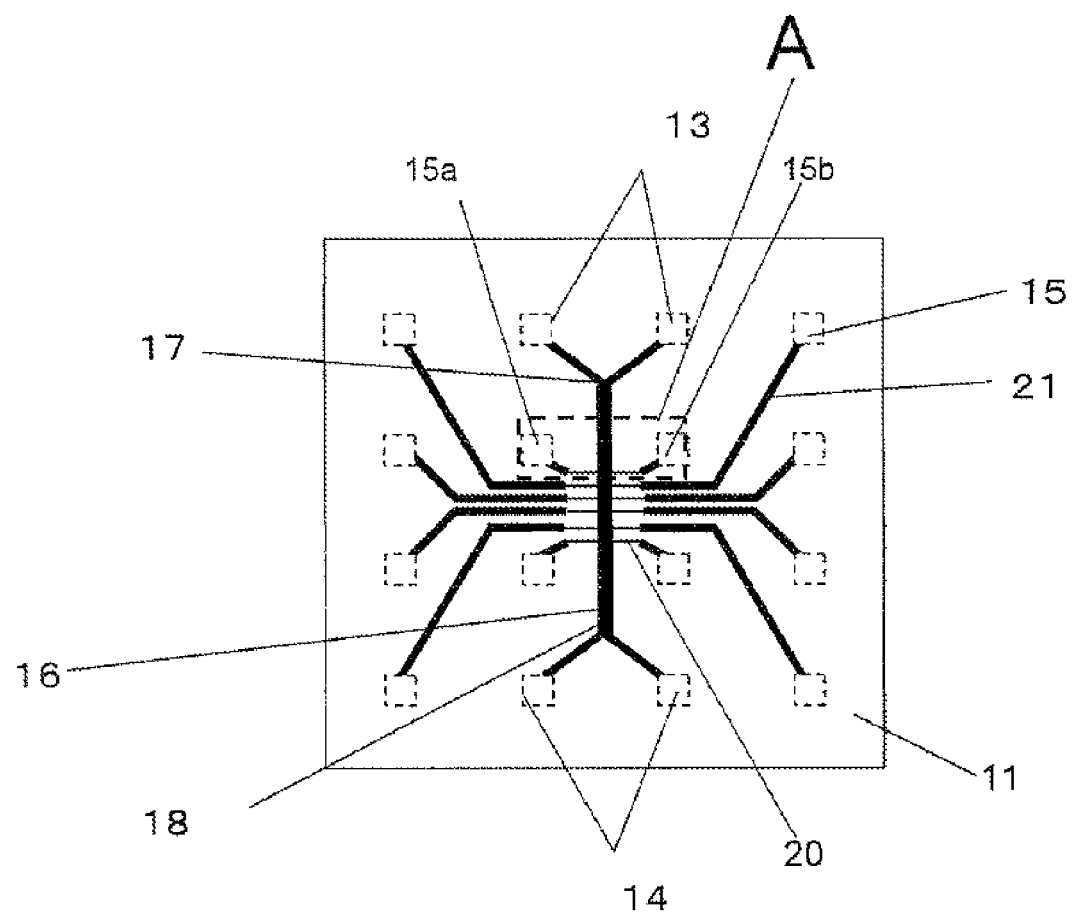
FIG. 2 is a transparent view of the measuring device according to the first embodiment, at its upper surface.
Figure 3:
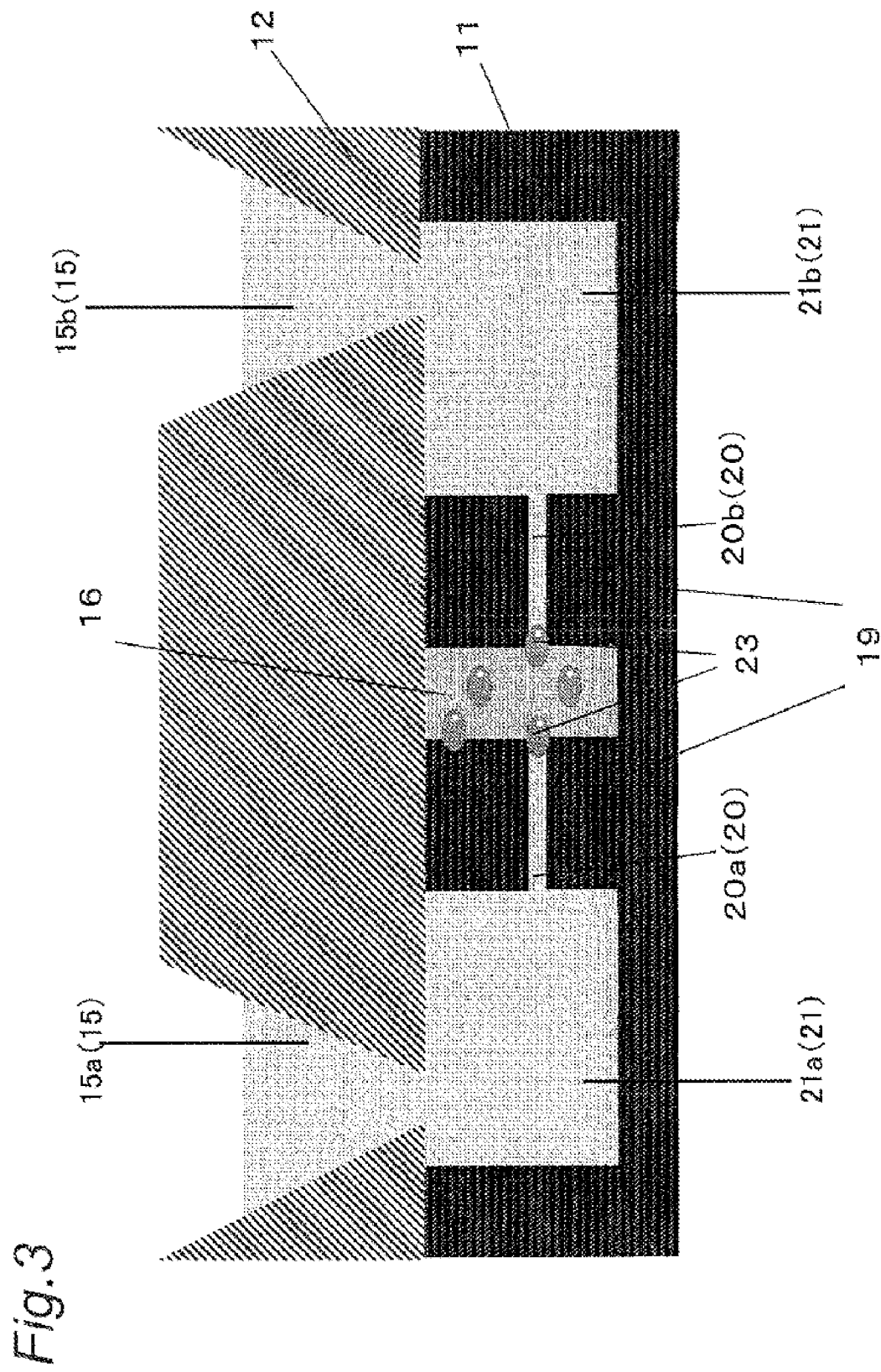
FIG. 3 is a cross-sectional view of a portion A in FIG. 2.

As illustrated in FIG. 1, the measuring device according to the present embodiment is constituted by a first substrate 11, and a second substrate 12 which is bonded on an upper portion of the first substrate 11 and is provided with inflow ports 13 at two positions, outflow ports 14 at two positions, and plural injection ports 15. Further, as illustrated in FIG. 2 and FIG. 3, these inflow ports 13 at the two positions and the outflow ports 14 at the two positions are all connected to each other through a first cavity 16, which is a slot portion formed in the first substrate 11, and the inflow ports 13 at the two positions are connected to the first cavity 16 through a two-branch-shaped first coupling portion 17, thereby enabling a solution or a chemical agent to be flowed into the first cavity 16. Further, the outflow ports 14 at the two positions are connected to the first cavity 16 through a two-branch-shaped second coupling portion 18, which enables the solution, chemical agent or the like to be flowed to the outflow ports 14 at the two positions. Further, the side surfaces of the first cavity 16 are constituted by partition wall portions 19 which are opposed to each other, wherein these partition wall portions 19 are provided with plural through holes 20 (20a, 20b) for trapping (capturing) objects 23 to-be-tested formed from cells or films derived from biological bodies, within the first cavity 16, and these plural through holes 20 (20a, 20b) are connected, independently of each other, with second cavities 21 (21a, 21b). Further, these respective second cavities 21 (21a, 21b) independently connect to the plural injection ports 15 (15a, 15b) formed in the second substrate 12, in order to connect to an external environment, independently of each other.

In this case, the partition wall portions 19 are structured to separate the first cavity 16 and the second cavities 21 (21a, 21b) from each other, and have no portion which connects the first cavity 16 and the second cavities 21 with each other, other than the through holes 20 (20a, 20b) provided in these partition wall portions 19. Further, there is no portion which directly connects each second cavity 21 with the other second cavities 21, like there is no portion which directly connects the second cavity 21a with the second cavity 21b and, thus, the second cavities 21 are formed independently of each other.

Further, the plural through holes 20 (20a, 20b) are formed at positions where the objects 23 to-be-tested introduced into the first cavity 16 cannot come into contact with the bottom surface or the upper surface of the first cavity 16. For example, in cases where the objects 23 to-be-tested are cells, preferably, the through holes 20 are formed at positions spaced apart from the bottom surface and the upper surface of the first cavity 16, by distances larger than about 10 to 20 micrometers, which corresponds to the size of the object 23 to-be-tested.

Further, the plural through holes 20 (20a, 20b) are used for trapping objects 23 to-be-tested at predetermined positions within the first cavity 16 and, therefore, the through holes 20 are formed to have a hole diameter smaller than the size of an object 23 to-be-tested. Preferably, they have a diameter in the range of 0.5 micrometer to 5.0 micrometers. Further, the positions, the length and the size of the through holes 20 (20a, 20b) can be properly changed according to the objects 23 to-be-tested employed therein.

Further, in the present embodiment, it is possible to employ silicon, quartz, glass or the like, as the material of the first substrate 11.

Further, as the material of the second substrate 12, it is possible to employ a silicon resin such as PDMS (polydimethylsiloxane), glass, silicon, quartz or the like. Particularly, such a PDMS resin is easy to shape and, also, has higher surface activity and, therefore, can be intimately and firmly contacted with the material of the first substrate 11, which is made of silicon, quartz, glass or the like, without employing an adhesive agent.

Next, there will be described a measuring method with the measuring device according to the present embodiment, by exemplifying a cell electrophysiological sensor as an example of the measuring device.

As illustrated in FIG. 2 and FIG. 3, a dispensing tool (not illustrated) is inserted into the inflow ports 13, and an extracellular fluid (an electrolytic solution) is injected therethrough such that it fills the inside of the entire first cavity 16. Next, dispensing tools (not illustrated) are inserted into the plural injection ports 15, and an intracellular fluid (an electrolytic solution) is injected therethrough such that it fills the insides of the respective second cavities 21.

In this case, in the case of muscle cells of a mammal, such an extracellular fluid is typically an electrolytic solution containing about 4 mM $K^+$ ions, about 145 mM $Na^+$ ions, and about 123 mM $Cl^-$ ions, while such an intracellular fluid is an electrolytic solution containing about 155 mM $K^+$ ions, about 12 mM $Na^+$ ions, and about 4.2 mM $Cl^-$ ions. An optimum chemical composition of them can be properly changed, according to the to-be-measured object and the aim of the measurement.

Figure 4:
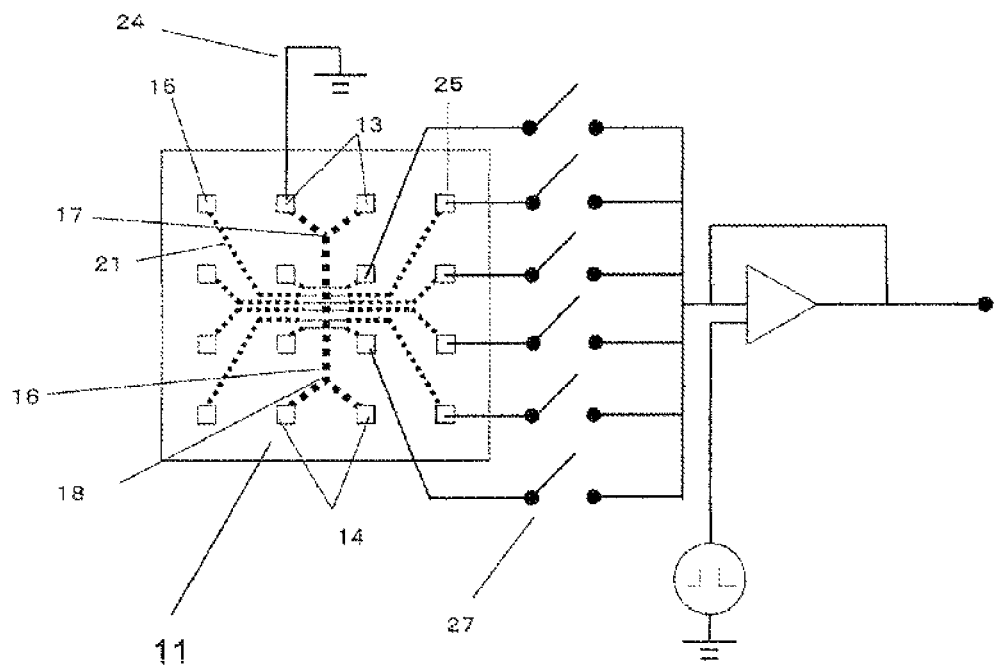
FIG. 4 is a main-part explanation view of the measuring device according to the first embodiment.
Figure 5:
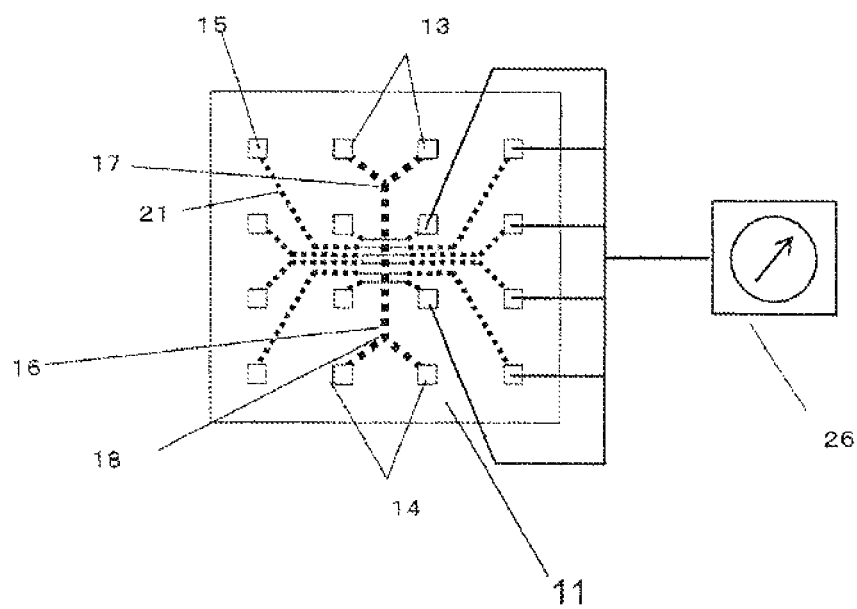
FIG. 5 is a main-part explanation view of the measuring device according to the first embodiment.

Next, as illustrated in FIG. 4, a reference electrode 24 is inserted into the extracellular fluid which fills the inflow ports 13 or the outflow ports 14, while measurement electrodes 25 are inserted into the intracellular fluid which fills the injection ports 15. Further, in this case, a suction device 26 is connected to the second cavities 21 in the intracellular-fluid side. Thus, it is possible to observe a conduction resistance value of about 100 k$\Omega$ to 20 M$\Omega$, between the reference electrode 24 electrically connected to the extracellular fluid and the measurement electrodes 25 electrically connected to the intracellular fluid. This is because the extracellular fluid or the intracellular fluid penetrates through the through holes 20, thereby forming an electric circuit between the reference electrode 24 and the measurement electrodes 25. Next, objects 23 to-be-tested suspended in the extracellular fluid are introduced thereinto through the inflow ports 13 through a dispensing tool (not illustrated) and, then, the pressures within the second cavities 21 are reduced through pressure transmission tubes with the common suction device 26 as illustrated in FIG. 5, so that the objects 23 to-be-tested are attracted by the opening portions 22 of the through holes 20 formed in the partition wall portions 19 at the side surfaces of the first cavity 16, and the objects 23 to-be-tested are trapped therein, as illustrated in FIG. 3 and FIG. 4. When objects 23 to-be-tested are closing the opening portions 22 of the through holes 20, if the objects 23 to-be-tested are absorbed in the through holes 20 with a higher adhesion force, this induces a state where the electric resistance between the extracellular fluid and the intracellular fluid is equal to or more than 1 GΩ and, thus, is extremely higher, wherein such a state indicates extremely-smaller electric leaks through the gaps between the through holes 20 and the objects 23 to-be-tested. This state is called giga-seal. In such a giga-seal state, it is possible to measure, with higher accuracy, electric-potential changes or electric-current passage induced intracellularly and extracellularly, due to electrophysiological actions of objects 23 to-be-tested, in a less-noise state. Accordingly, before measurement of electrophysiological reactions of objects 23 to-be-tested, there is a process for determining the electric resistances between the extracellular fluid within the first cavity 16 and the intracellular fluids introduced in the respective second cavities 21, in order to determine whether or not there have been formed individual giga-seal states therein.

Further, in the aforementioned example, the measurement is performed by filling the first cavity 16 with the extracellular fluid, and filling the second cavities 21 with the intracellular fluid and, thereafter, introducing objects 23 to-be-tested into the first cavity 16, in the mentioned order. The measurement is not restricted in the above order. The measurement can be also performed by introducing, firstly, an intracellular fluid into the first cavity 16, and also employing a solution for suspending cells as the intracellular fluid into the first cavity 16, further introducing the cells into the first cavity 16 and, then, causing the cells to be absorbed in the through holes 20 and, thereafter, introducing an extracellular fluid thereinto through the inflow ports 13 to change the content of the first cavity 16 from the intracellular fluid to the extracellular fluid, in the mentioned order. This is for the following reason. If, firstly, the extracellular fluid is introduced into the first cavity 16 and the intracellular fluid is introduced into the second cavities 21, respectively, one of the solutions may be mixed into the other one, which may change the solution composition around the objects 23 to-be-tested, thereby preventing correct measurement. In order to avoid mixing the solutions and changing the solution composition around the objects 23 to-be-tested, it is possible to employ the aforementioned order of introductions.

Thereafter, a chemical agent is injected thereinto through the inflow ports 13 with a dispensing tool (not illustrated), in order to stimulate the objects 23 to-be-tested. In this case, as a method for stimulating the objects 23 to-be-tested, it is possible to employ either a chemical stimulation using a chemical agent and the like as in the present embodiment or a physical stimulation using electric signals created between the reference electrode 24 and the measurement electrodes 25. Further, if a physicochemical reaction is caused in the objects 23 to-be-tested, in response to such chemical or physical stimulation, the physicochemical reaction can be detected, based on the electric-potential differences between the reference electrode 24 and the measurement electrodes 25 (or electric-current value changes or resistance-value changes therebetween).

Figure 6:
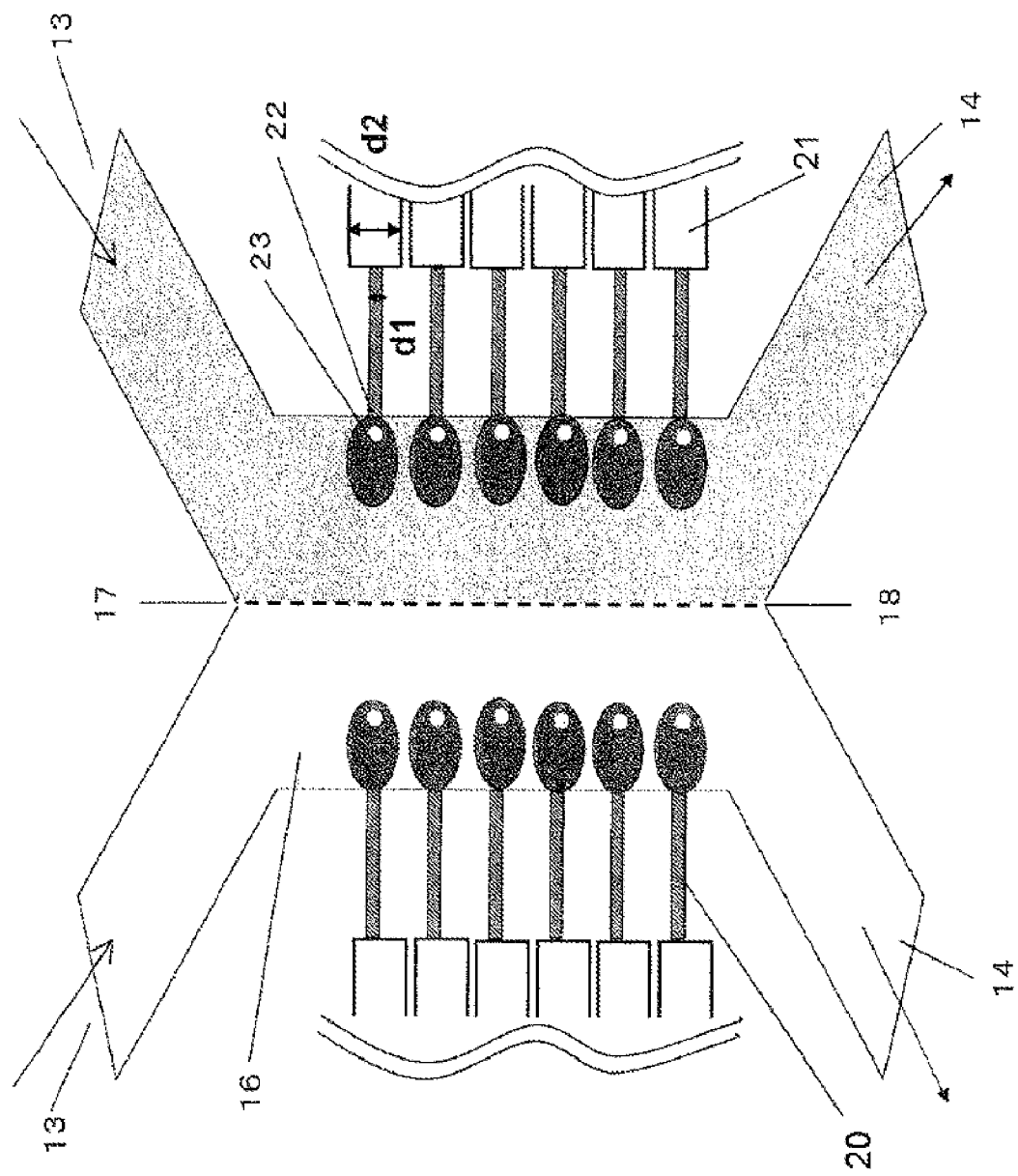
FIG. 6 is a main-part explanation view of the measuring device according to the first embodiment.

Further, at this time, as illustrated in FIG. 6, different solutions can be flowed thereinto through the respective inflow ports 13 at the two positions, and each of these different solutions can be flowed along one of the side walls of the first cavity 21, which enables performing measurements on these different solutions respectively at the same time. Thus, if a physicochemical reaction is caused in the objects 23 to-be-tested, this reaction can be detected, based on the electric-potential differences between the reference electrode 24 and the measurement electrodes 25 (or electric-current value changes or resistance-value changes therebetween).

Hereinafter, effects of the present embodiment will be described.

According to the present embodiment, it is possible to improve the measurement efficiency of the measuring device. This is because measurement can be performed independently on the respective objects 23 to-be-tested trapped in the plural through holes 20.

Namely, in the present embodiment, there are provided the plural independent second cavities 21, wherein there is no portion which directly connects each second cavity 21 with the other second cavities 21 and, thus, these second cavities 21 are independent of each other. Accordingly, after objects 23 to-be-tested flowed into the first cavity 16 have been trapped into the opening portions 22 of the respective through holes 20, by determining the impedances between the reference electrode 24 and the measurement electrodes 25, it is possible to independently make determinations of the presence or absence of adhesion failures, such as determinations as to whether or not objects 23 to-be-tested are certainly being trapped in the opening portions 22 of the respective through holes 20. This enables easily finding through holes 20 inducing electric leaks therethrough. Also, it is possible to independently make determinations of the presence or absence of absorption errors, such as determinations as to whether or not unactivated objects 23 to-be-tested are being trapped in the opening portion 22 of the through holes 20 or just dust, rather than objects 23 to-be-tested, is being trapped therein. This enables selecting through holes 20 in which objects 23 to-be-tested are being certainly trapped. Further, as illustrated in FIG. 4, the individual measurement electrodes 25 provided in the respective second cavities 21 are connected to switches 27, which enables cutting off and connecting the measurement electrodes 25 therefrom and thereto, after checking the results of previous determinations. This enables connecting the measurement electrodes 25 thereto, only for the selected through holes 20. Further, by using the measurement electrodes 25 connected thereto for measurement through a pharmacologic stimulus, it is possible to perform measurement with higher accuracy.

Further, in the present embodiment, the through holes 20 are provided at positions where the objects 23 to-be-tested introduced into the first cavity 16 can not come into contact with the bottom surface and the upper surface of the first cavity 16. For example, in the case of employing cells as objects 23 to-be-tested, in general, such cells are floated within the extracellular fluid, and these floating cells exist at a center portion of the inside of the cavity at a higher density than those around the wall surfaces thereof. Accordingly, since the through holes 20 are at positions which are higher than the bottom surface of the cavity but lower than the upper surface thereof, it is possible to facilitate trapping of floating cells therein. Further, the through holes 20 are provided at a height larger than the size of an object 23 to-be-tested, which can inhibit the objects 23 to-be-tested having been trapped therein from being obstructed by the bottom surface.

Further, in the present embodiment, there are provided at least two inflow ports 13 and at least two outflow ports 14. This enables flowing a chemical-agent candidate compound into the first cavity 16 through one of the inflow ports 13 while flowing, thereinto, an extracellular fluid which does not contain the aforementioned chemical-agent candidate compound through another inflow port 13, such that these solutions of different types are in a laminar-flow state where they are not mixed with each other within the first cavity 16. Accordingly, it is possible to measure, at the same time, reactions of cells trapped in the through holes 20 in one side, to the chemical-agent candidate compound, and reactions of cells in the through holes 20 in one side, to the extracellular fluid which does not contain the aforementioned chemical-agent candidate compound, thereby enabling making, more accurately, comparisons between electrochemical signals generated from the cells. Accordingly, it is possible to perform measurement for different solutions through single measurement, thereby smoothly performing chemical-agent stimuli.

Further, in the present embodiment, PDMS, which is a resin with higher transparency, is employed, as the material of the second substrate 12. This enables individually and visually making determinations of the presence or absence of absorption errors, such as determinations as to whether just dust, rather than objects 23 to-be-tested, is being trapped in the opening portions 22 of the through holes 20. Further, in the case of employing cells as objects 23 to-be-tested, for example, it is possible to perform labeling on these cells with a fluorescent agent, which makes it easier to make such visual determinations.

Further, it is desirable that the side walls of the first cavity 16 are formed from the partition wall portions 19, and that the side walls are in parallel with each other, which can make the measurement efficiency higher.

Further, the width of the first cavity 16 is preferably uniform from the coupling portion between the inflow ports 13 at the two portions and the coupling portion between the outflow ports 14 at the two positions, which enables maintaining a uniform laminar-flow state.

Further, the first cavity 16 is preferably formed to have a width larger than at least twice the size of an object 23 to-be-tested. Therefore, the measurement can not be influenced by other trapped objects 23 to-be-tested, when objects 23 to-be-tested have been trapped in the through holes 20 opposing to each other.

Further, as illustrated in FIG. 6, the width of the first cavity 16 is desirably about twice the width of each outflow port 14 or inflow port 13, which enables maintaining the pressures of the liquids opposing to each other, thereby facilitating formation of laminar flows in the first cavity 16.

Further, the first coupling portion 17 and the second coupling portion 18 are desirably shaped to facilitate formation of laminar flows within the first cavity, and they preferably have a Y-shape or a T-shape.

Further, the opening portions 22 of the plural through holes 20 provided in the side walls of the first cavity 16 are preferably opposed to each other, in these side walls. This is for the following reason. In this case, when plural solutions are flowed thereinto in a laminar-flow state, it is possible to perform measurement on objects 23 to-be-tested trapped in these through holes 20 opposing to each other, to synchronize the timings of inflows of these solutions with each other.

Further, the respective through holes 20 are preferably placed at intervals equal to or larger than at least the size of an object 23 to-be-tested, in view of certainly trapping objects 23 to-be-tested therein.

Further, as illustrated in FIG. 6, it is preferable that each second cavity 21 has an upper cross-sectional diameter larger than the through-hole upper cross-sectional diameter of the through holes 20. Namely, it is preferable that the hole diameter (d1) of the through holes 20 which are provided in the partition wall portions 19 and penetrate therethrough from the first cavity 16 to the second cavities 21 is smaller than the hole diameter (d2) of the second cavities 21 connected thereto. Namely, there is the relationship between the hole diameter (d1 and d2) as equation of d2>d1.

By forming the aforementioned shape which satisfies the aforementioned relational expression, it is possible to facilitate suction from the second cavities 21, when objects 23 to-be-tested flowing through the first cavity 16 are trapped into the through holes 20. This can certainly bring objects 23 to-be-tested into intimate contact with the opening portions 22 of the through holes 20. Further, in the case of employing cells as objects 23 to-be-tested, a chemical agent such as amphotericin or nystatin may be employed in some cases, and such a chemical agent injected through the second cavities 21 can be easily flowed into the through holes 20, which allows it to rapidly reach cells as objects 23 to-be-tested.

Further, more preferably, the plural through holes 20 placed in the side surfaces of the first cavity 16 are formed near a midway portion of the first cavity 16. This is because there is a concern about the following situation. When different chemical agents are flowed thereinto through the inflow ports 13 at the two positions, if these chemical agents have different diffusion coefficients, it may cause these chemical agents to have different concentrations in an upstream portion and a downstream portion of the first cavity 16. Accordingly, in order to perform measurement with uniform concentrations, it is preferable that the plural through holes 20 are formed such that they are close to one another within the first cavity 16.

Here, this is regarding the positions of the opening portions 22 of the through holes 20, and the through holes 20 can be placed to have any hole shape toward the second cavities 21. Namely, the hole shapes of the through holes 20 can be such that they are placed either orthogonally or obliquely with respect to the first cavity 16.

Further, in the present embodiment, the inflow ports 13 and the outflow ports 14 are both provided at two positions, but it is desirable that they are both provided at two or more positions. This is because provision of them at two or more positions enables utilization of various measurement methods. Further, it is desirable that the number of inflow ports 13 is equal to the number of outflow ports 14.

Further, in the case of employing cells as objects 23 to-be-tested, it is necessary to form holes in cell membranes being trapped in the opening portions 22 of the through holes 20 and, thus, closing the through holes 20, namely it is necessary to form whole cell. In such a case, it is possible to employ a method for injecting a chemical agent, such as nystatin, through the injection ports 15 into second cavities 21 having been determined to create a giga-seal state, a method for performing suction from these second cavities 21, or other methods, in order to form holes in the cell membranes closing the through holes 20.

Further, the suction device 26 connected to the second cavities 21 can be a common suction device 26 connected thereto as illustrated in FIG. 5 or can also be those independently connected to the respective second cavities 21. This is because provision of such respective independent suction devices 26 enables performing suction only on a single second cavity 21. Also, it is desirable to employ a common suction device, which enables concurrent control and realizes excellent convenience.

Further, as illustrated in FIG. 4, the measurement electrodes 25 are connected to the respective switches 27, which enables cutting off or connecting the measurement electrodes 25 therefrom and thereto and, also, enables connecting other measurement electrodes 25 thereto. This makes it easier to combine individual results from these respective measurement electrodes 25, thereby making it easier to visually recognize electric changes.

Further, as illustrated in FIG. 4, the reference electrode 24 is inserted through the inflow ports 13, but it can be inserted through either the inflow ports 13 or the outflow ports 14.

Second Embodiment

There will be described the structure of a measuring device according to the present embodiment. Further, the same portions as the portions described in the first embodiment will not be described herein. The present embodiment is different from the first embodiment, in terms of the opening diameter of through holes 20.

Figure 7:
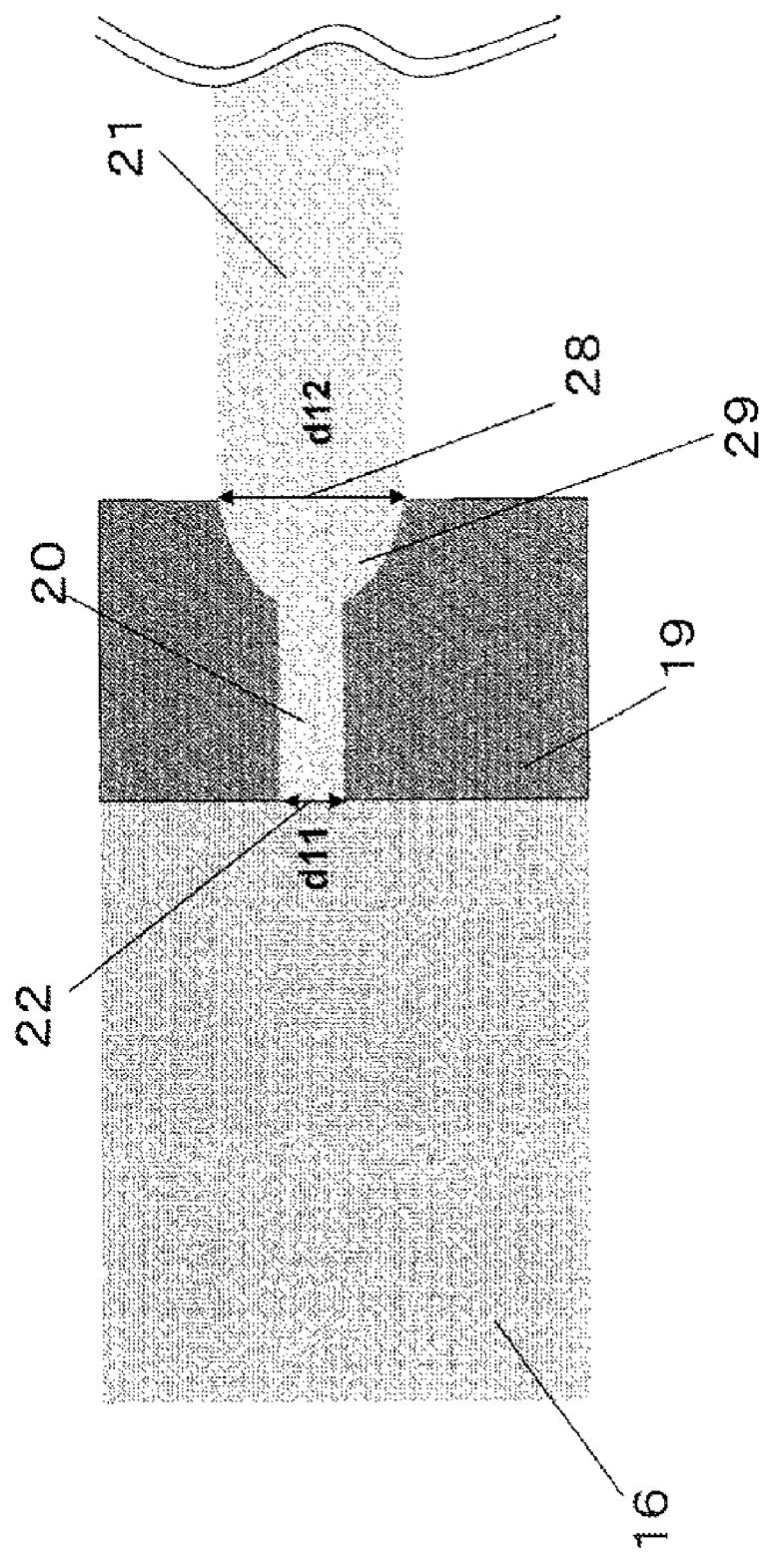
FIG. 7 is a main-part explanation view of a measuring device according to a second embodiment.
Figure 8:
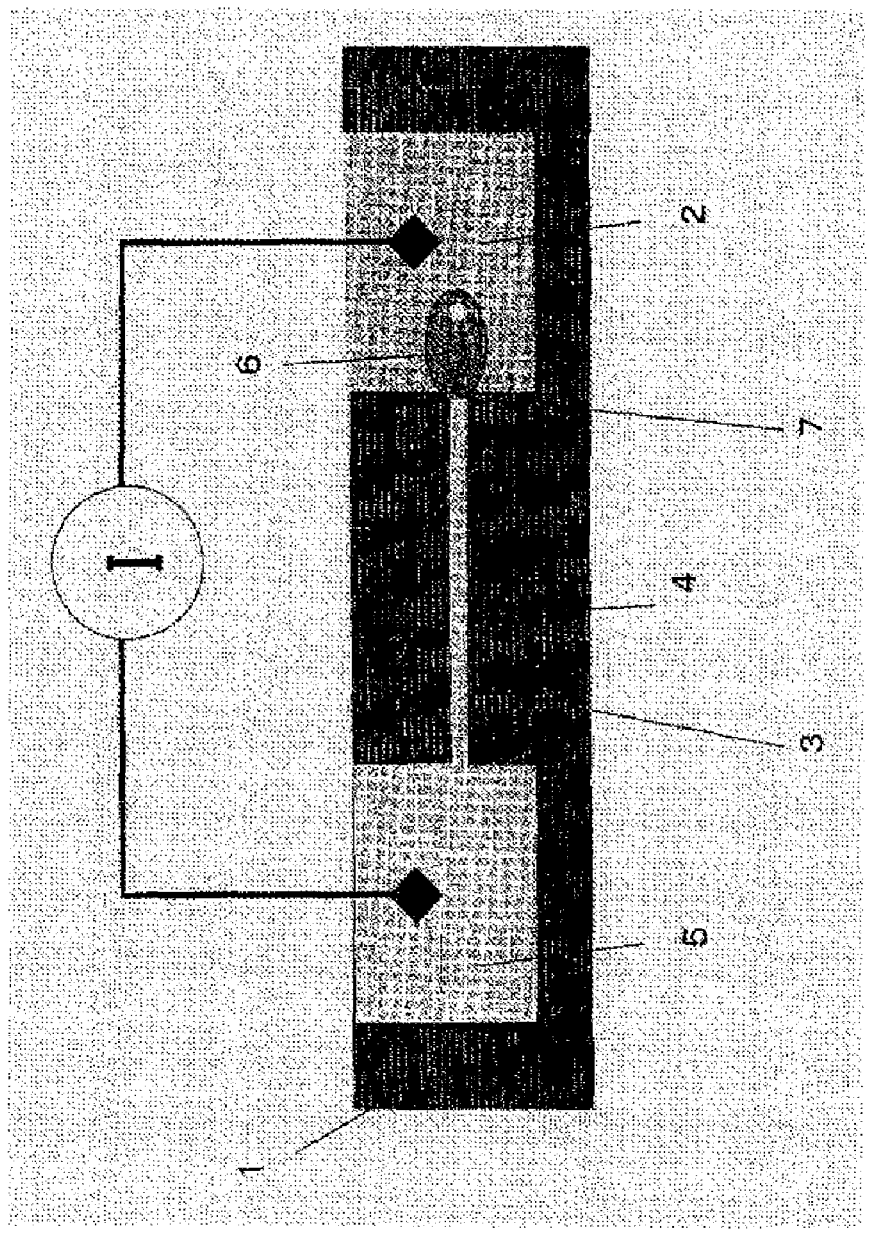
FIG. 8 illustrates a conventional measuring device.

FIG. 7 is a main-part explanation view illustrating the structure of a through hole in the measuring device according to the present embodiment.

As illustrated in FIG. 7, the through hole 20 which is provided in a partition wall portion 19 and penetrates therethrough from a first cavity 16 to a second cavity 21 has opening diameters having such sizes that the opening diameter (d12) of the opening portion 28 facing the second cavity 21 is larger than the opening diameter (d11) of the opening portion 22 facing the first cavity 16. Namely, there is the relationship between the opening diameter (d11 and d12) as equation of d12>d11.

In order to certainly trap an object 23 to-be-tested into the through hole 20, it is necessary to form the through hole 20 to be smaller and thinner than the size of the object 23 to-be-tested. However, if such a smaller and thinner through hole is made to have a larger length, it may increase the resistance value, thereby making it difficult to apply an accurate voltage to the object 23 to-be-tested. Also, in the case of performing suction using the suction device 26 from the second cavity 21 as illustrated in FIG. 5, in order to trap an object 23 to-be-tested into the through hole 20, if such a smaller and thinner through hole 20 has a larger length, it may cause a larger pressure loss in the suction pressure, such that the object 23 to-be-tested can not be sufficiently sucked therethrough, thereby making it hard to certainly trap it.

By forming the aforementioned shape, it is possible to facilitate suction from the second cavity 21, when an object 23 to-be-tested flowing through the first cavity 16 is trapped into the through hole 20. This enables certainly bringing the object 23 to-be-tested into intimate contact with the opening portion 22 of the through hole 20. Further, in the case of employing cells as objects 23 to-be-tested, a chemical agent such as amphotericin or nystatin may be employed in some cases, and such a chemical agent injected through the second cavity 21 can be easily flowed into the through hole 20, which allows it to rapidly reach cells as objects 23 to-be-tested.

Further, in the present embodiment, the through hole 20 is provided in the partition wall portion 19 and penetrates therethrough from the first cavity 16 to the second cavity 21. The through hole 20 has opening diameters with sizes having such a relationship that the opening diameter (d12) of the opening portion 28 facing the second cavity 21 is larger than the opening diameter (d11) of the opening portion 22 facing the first cavity 16. However, the relationship therebetween is not limited thereto. For example, the through hole 20 can be also formed to have upper cross-sectional diameters which gradually increase from the opening diameter (d11) of the opening portion 22 facing the first cavity 16 to the opening diameter (d12) of the opening portion 28 facing the second cavity 21, which can also offer the same effects.

Further, it is desirable that the through hole 20 is further provided with a concave portion 29 from the opening portion 28 facing the second cavity 21 toward the aforementioned first cavity 16. This can offer effects of the concave portion 29 as will be described later, while certainly trapping an object 23 to-be-tested with the smaller diameter of the opening portion 22 of the through hole 20 facing the first cavity 16, thereby enabling measurement with higher efficiency.

It is desirable that an object 23 to-be-tested is trapped into a thinner through hole 20. Therefore, as illustrated in FIG. 7, in an example of the present second embodiment, the through hole 20 is formed to be straight (to have the same hole diameter) from the beginning (near the first cavity 16) to a midway portion thereof and, thereafter, is provided with the concave portion 29 toward the second cavity 21, rather than being shaped to have gradually-increasing hole diameters. As described above, by providing the through hole 20 with the straight thinner hole having the same diameter from the first cavity 16 side to a midway portion thereof, it is possible to improve the rate of trapping of objects 23 to-be-tested. On the other hand, by providing the concave portion 29 toward the second cavity 21, it is possible to offer the effect of facilitating suction through the concave portion 29, from the midway portion to the second cavity 21.

With the present invention, it is possible to realize a measuring device which enables smooth measurement of pharmacologic reactions with higher measurement efficiency.

DESCRIPTION OF REFERENCE SIGNS

11 First substrate
12 Second substrate
13 Inflow port
14 Outflow port
15 Injection port
16 First cavity
17 First coupling portion
18 Second coupling portion
19 Partition wall portion
20 Through hole
21 Second cavity
22 Opening portion
23 Object to-be-tested
24 Reference electrode
25 Measurement electrode
26 Suction device
27 Switch
28 Opening portion
29 Concave portion

The invention claimed is:
1. A measuring device comprising:
a first substrate;
a second substrate bonded on the first substrate, the second substrate having at least two inflow ports, at least two outflow ports, and a injection port, wherein the two inflow ports, the two outflow ports, and the injection port penetrate the second substrate, wherein the first substrate includes:
- partition wall portions opposing to each other, and forming a first cavity between the partition wall portions, a first solution being stored within the first cavity, and forming at least two second cavities close against one of the partition wall portions, wherein each second cavity is provided adjacent to the first cavity, a second solution being stored within the respective second cavities independently of each other; and
- through holes provided in the respective partition wall portions to connect the first cavity and the second cavity to each other, and the through holes being adapted to capture an object to-be-tested introduced in the first cavity, the through holes being provided at a position where an object to-be-tested introduced into the first cavity cannot come into contact with a bottom surface and an upper surface of the first cavity, the measuring device further comprising:
- a first electrode in contact with the first solution; and
- a second electrode in contact with the second solution, whereby an electric-potential difference between the first electrode and the second electrode is determined, wherein the first cavity is connected to an external environment through the two inflow ports and the two outflow ports, and the second cavity is connected to the external environment through the injection port.

2. The measuring device according to claim 1, wherein the first cavity has side walls with through holes, such that the side walls having the through holes are parallel with each other.

3. The measuring device according to claim 2, wherein the through holes have respective opening portions facing each other through the first cavity.

4. The measuring device according to claim 1, wherein each of different solutions can be flowed along one of the side walls of the first cavity through one of the two inflow ports, whereby measurements on the different solutions can be performed at the same time.

5. The measuring device according to claim 1, wherein the injection port is connected to a common suction device.

6. The measuring device according to claim 1, wherein each of the through holes has one opening portion facing the first cavity and another opening portion facing the second cavity, such that the opening diameter of the opening portion facing the second cavities is larger than the opening diameter of the opening portions facing the first cavity.

7. The measuring device according to claim 6, wherein each of the through holes has a concave portion toward the first cavity, the concave portion starting with the opening diameter of the opening portion facing the second cavity.

8. The measuring device according to claim 1, wherein the second electrodes are connected to respective switch selection devices, respectively, so as to allow selection of a connecting state or a cutting-off state between the second electrode and a measurement-signal amplifier with every second electrode.

* * * * *